(12) United States Patent
Gregg et al.

(10) Patent No.: US 10,285,612 B2
(45) Date of Patent: May 14, 2019

(54) USER FEEDBACK TO CONTROLS ISCHEMIA MONITORING ECG ALGORITHM

(71) Applicant: KONINKLIJKE PHILIPS N.V., Eindhoven (NL)

(72) Inventors: Richard E. Gregg, Andover, MA (US); Volker Manfred Hubert, Gaertringen (DE); Sophia Huai Zhou, Cambridge, MA (US); Saeed Babaeizadeh, Arlington, VA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 58 days.

(21) Appl. No.: 15/507,429

(22) PCT Filed: Aug. 31, 2015

(86) PCT No.: PCT/IB2015/056594
§ 371 (c)(1),
(2) Date: Feb. 28, 2017

(87) PCT Pub. No.: WO2016/035000
PCT Pub. Date: Mar. 10, 2016

(65) Prior Publication Data
US 2017/0281277 A1    Oct. 5, 2017

Related U.S. Application Data

(60) Provisional application No. 62/044,469, filed on Sep. 2, 2014.

(51) Int. Cl.
A61B 5/04      (2006.01)
A61B 5/0452   (2006.01)
A61B 5/00      (2006.01)

(52) U.S. Cl.
CPC .......... *A61B 5/0452* (2013.01); *A61B 5/7203* (2013.01); *A61B 5/746* (2013.01);
(Continued)

(58) Field of Classification Search
CPC ..... A61B 5/0452; A61B 5/7203; A61B 5/746; A61B 5/7475; A61B 5/7264; A61B 5/7221
See application file for complete search history.

(56) References Cited

U.S. PATENT DOCUMENTS 6,609,023 B1   8/2003   Fischell et al.
8,452,404 B1   5/2013   Fischell et al.
(Continued)

FOREIGN PATENT DOCUMENTS

WO    9955228 A1      11/1999
WO    2007130217 A1   11/2007
(Continued)

*Primary Examiner* — Amanda K Hulbert
*Assistant Examiner* — Natasha Patel

(57) ABSTRACT

When detecting ischemia and/or myocardial infarction in a subject, electrocardiogram (ECG) segments are analyzed for elevated ST segments indicative of ischemia and/or infarction. To mitigate false positive alerts, an ECG segment comprising an elevated ST segment that triggers an alert is presented to a clinician for verification as being indicative of ischemia or infarction, or as being attributable to a confounding condition not indicative of ischemia or infarction. Clinician feedback is used to adjust an elevated ST segment detection algorithm to improve accuracy and mitigate false positive alerts.

19 Claims, 5 Drawing Sheets

(52) U.S. Cl.
CPC ........... *A61B 5/7221* (2013.01); *A61B 5/7264* (2013.01); *A61B 5/7475* (2013.01)

(56) References Cited

U.S. PATENT DOCUMENTS

| | | |
|---|---|---|
| 2004/0122790 A1 | 6/2004 | Walker et al. |
| 2008/0162183 A1 | 7/2008 | Sachanandani et al. |
| 2009/0216141 A1 | 8/2009 | Fischell et al. |
| 2012/0053473 A1 | 3/2012 | Johnson et al. |
| 2012/0136266 A1 | 5/2012 | Grady |
| 2013/0096447 A1 | 4/2013 | Dhawan et al. |
| 2014/0058742 A1 | 2/2014 | Chari et al. |
| 2014/0081162 A1 | 3/2014 | Snell et al. |
| 2016/0045166 A1* | 2/2016 | Gheeraert .......... A61B 5/04011 600/509 |
| 2016/0135706 A1* | 5/2016 | Sullivan ............... A61B 5/0059 600/301 |

FOREIGN PATENT DOCUMENTS

| | | |
|---|---|---|
| WO | 2011093919 A1 | 8/2011 |
| WO | 2013054242 A1 | 4/2013 |

\* cited by examiner

USER FEEDBACK TO CONTROLS ISCHEMIA MONITORING ECG ALGORITHM

CROSS-REFERENCE TO PRIOR APPLICATIONS

This application is the U.S. National Phase application under 35 U.S.C. § 371 of International Application No. PCT/IB2015/056594, filed on Aug. 31, 2015, which claims the benefit of U.S. Provisional Patent Application No. 62/044,469, filed on Sep. 2, 2014. These applications are hereby incorporated by reference herein.

The present innovation finds application in detection of myocardial infarction and ischemia in a subject, particularly with regard to ST segment elevation therein. However, it will be appreciated that the described techniques may also find application in other electrocardiogram (ECG) monitoring systems, other patient monitoring scenarios, other ECG evaluation techniques, and the like.

Cardiac ischemia due to a complete blockage of a coronary artery can be detected in an ECG from an elevated ST-segment. The elevated ST-segment is due to injury current between the healthy part of the heart muscle and the ischemic part, which is receiving reduced blood supply. Cardiac ischemia monitoring is often called ST monitoring because the ST-segment voltage is the main parameter used to generate an alarm.

The present application provides new and improved systems and methods that facilitate reducing false positive ST monitoring alerts by training an ischemia monitoring classifier or algorithm using feedback from a user, which overcome the above-referenced problems and others.

In accordance with one aspect, a method of mitigating false positive alerts for ischemic ECG patterns (including elevated or depressed ST segments, inverted T-waves, pathologic Q-waves, reduced R-waves or changes in these measures) in an electrocardiogram (ECG) indicative of ischemia or myocardial infarction comprises receiving real-time ECG data, measuring a level of noise associated with each of a plurality of ECG segments, and identifying a lowest-noise ECG segment, which has a lowest level of noise relative to other ECG segments in the plurality of ECG segments. The method further comprises analyzing the lowest-noise ECG segment to detect one or more ischemic ECG patterns therein, upon detection of the one or more ischemic ECG patterns, generating an alert, and presenting the lowest-noise ECG segment that triggered the alert to a user for review. Additionally, the method comprises receiving user feedback regarding whether the alert is a false positive, and adjusting an ischemia and acute infarction detection algorithm as a function of the received user input such that elevated ST segments and/or other features of ischemic ECG patterns not indicative of ischemia or myocardial infarction are ignored.

According to another aspect, a system that facilitates mitigating false positive alerts when monitoring ST elevation and other ECG features in an electrocardiogram (ECG) indicative of ischemia or myocardial infarction comprises a noise measuring module that receives real-time ECG data and measures a level of noise associated with each of a plurality of ECG segments, and a best periodic ECG identifying module that receives the real-time ECG data and noise measurement information from the noise measuring module, and identifies a lowest-noise ECG segment, which has a lowest level of noise relative to other ECG segments in the plurality of ECG segments. The system further comprises an ECG analysis module that analyzes the lowest-noise ECG segment to detect one or more elevated ST segments therein, and an alert generator that generates an alert upon detection of the one or more elevated ST segments. Additionally, the system comprises a user interface on which the lowest-noise ECG segment that triggered the alert is presented to a user for review and via which the alert generator receives user feedback regarding whether the alert is a false positive, and a processor that adjusts an elevated ST segment detection algorithm as a function of the received user input such that elevated ST segments not indicative of ischemia or myocardial infarction are ignored.

According to another aspect, an alert generator device that generates alerts indicative of ischemia or myocardial infarction upon detection of ischemic patterns in an electrocardiogram (ECG) comprises at least one measurement buffer that receives current ECG segment measurements and ischemic ECG feature information, an ischemic feature change detection module that receives the current ECG segment measurements and ischemic ECG pattern information and receives delayed measurements and ischemic feature information from the buffer for comparison, and an infarct and ischemia detection module that receives the current ECG segment measurements and ischemic pattern information and detects an ischemic pattern. The alert generator device further comprises a median filter or smoothing filter that receives and combines change in ischemic pattern information from the ischemic pattern change module and the detected ischemic patterns from the infarct and ischemia detection module, and generates an alert as a function of the received outputs, and an infarct and ischemia noise scoring module that generates a probability indicative of a likelihood that the detected ischemic pattern is indicative of an ischemic or infarction event and outputs a predetermined ECG sample segment to a user interface for user confirmation that the alert is not a false positive.

One advantage is that ischemia and myocardial infarction detection is improved by using ECG features beyond ST elevation or depression and also changes in those features.

Another advantage is that false positive alerts are reduced.

Still further advantages of the subject innovation will be appreciated by those of ordinary skill in the art upon reading and understand the following detailed description.

The drawings are only for purposes of illustrating various aspects and are not to be construed as limiting.

The described systems and methods overcome the above-mentioned problems by reducing false positive ischemia alerts when monitoring for ischemia in a patient. In one embodiment, an ischemia and infarction monitoring algorithm is trained using user feedback to recognize elevated or depressed ST waveforms and other ECG patterns that mimic waveforms indicative of ischemia but which do not in fact indicate ischemia.

For instance, conditions outside of cardiac ischemia that cause ST elevation and other ischemic patterns are not always detected by conventional automated algorithms, but the conditions may be diagnosed by a clinician. The clinician may have additional information not available to the automated algorithm or the clinician may recognize the ECG pattern for the confounding condition causing the false positive ECG pattern. When the algorithm detects ST elevation, depression or other features mimicking ischemia due to one of these confounding (non-ischemic) conditions, the resulting monitoring alert is false. In accordance with the present innovation, the algorithm receives feedback about an alternate cause of the ST-segment elevation or depression, and the algorithm behavior is altered specifically for that feedback. In one embodiment, to reduce false positive alerts the algorithm is trained to stop alerting on absolute ST elevation but rather alert on changes in ST elevation (relative ST elevation). Another example of an alteration to algorithm behavior is to reset the baseline ST values used for absolute ST thresholds to the ST values found at the time of the user feedback, which will also reduce the number of false positive alerts. For example, the baseline ST values may be zero, and ST thresholds may be 100 uV. When the ST values are reset, the baseline value changes from zero to the current value so that an absolute ST alert occurs when the ST value is increased from that non-zero baseline value.

Figure 1:
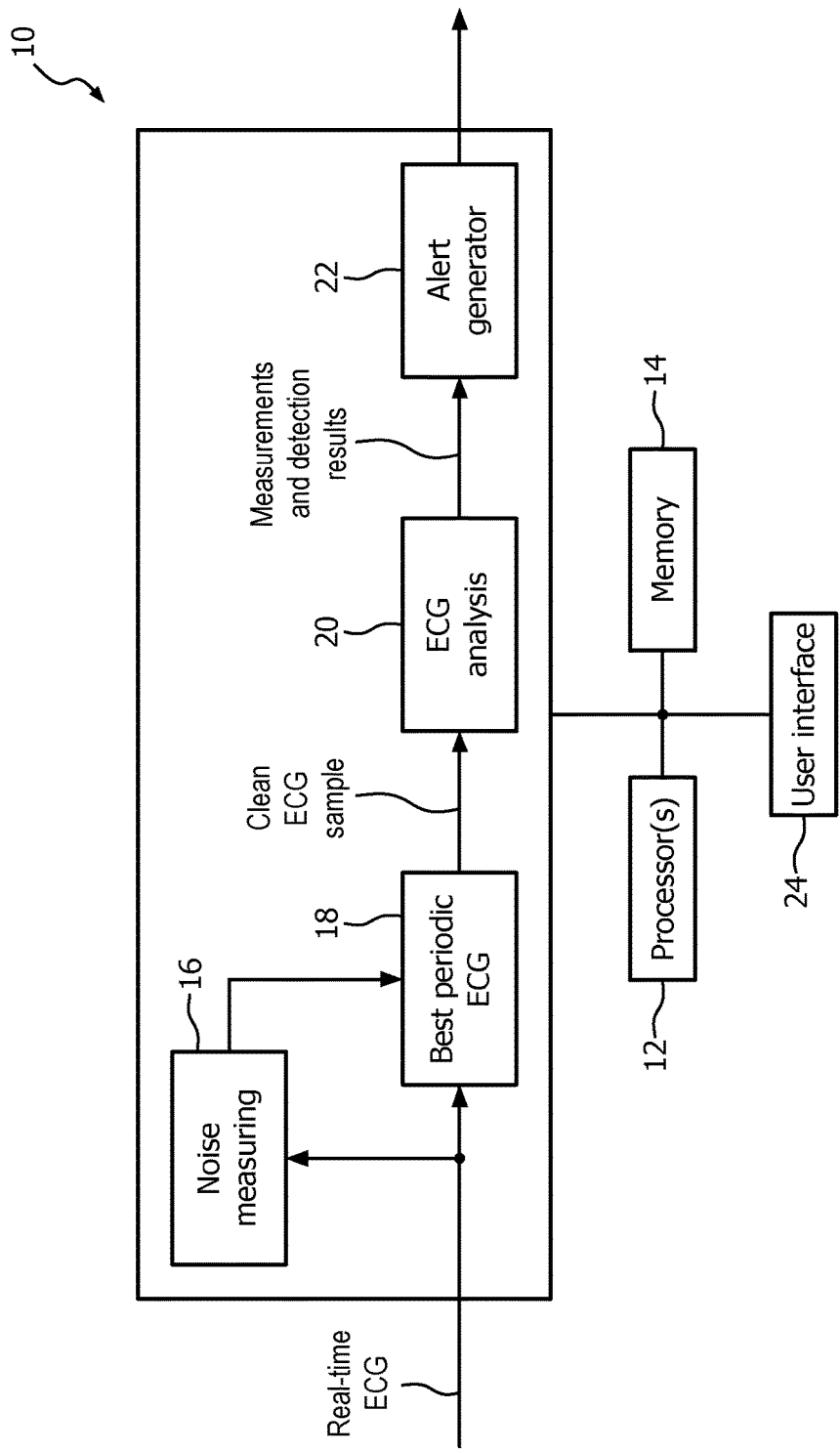
FIG. 1 illustrates an ischemia/infarction monitoring system that facilitates reducing false positive ischemia alerts when monitoring for ischemia in a patient, in accordance with one or more features described herein.

FIG. 1 illustrates an ischemia monitoring system 10 that facilitates reducing false positive ischemia alerts when monitoring for ischemia in a patient, in accordance with one or more features described herein. The figure shows a block diagram of the ischemia monitoring system 10, comprising a processor 12 that executes, and a memory 14 stores, computer-executable instructions for performing the various functions, methods, techniques, applications, etc., described herein. Real-time ECG data is scored by a noise measuring module 16, which is executed by the processor 12, according to an amount of noise detected in the ECG signal. The lowest-noise ECG segments or "strips" are identified by a best periodic ECG module 18, which is also executed by the processor. The processor further executes an ECG analysis module 20 that analyzes the lowest-noise ECG segments to determine whether a combination of ECG measurements is indicative of an ischemic event or an infarction event. The measurements and ischemia/infarction detection results are passed on to an alert generator 22, which generates an alert when the results indicate that an ischemic or infarction event has occurred.

It will be understood that the processor 14 executes, and the memory 16 stores, computer executable instructions for carrying out the various functions and/or methods described herein. The memory 16 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 14 can read and execute. In this context, the system 10 may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphics processing unit (GPU), or PAL, or the like.

According to one embodiment, feedback from a user (e.g., a clinician) in the form of a selection from a drop down list of diagnoses presented to the user on a user interface 24 (e.g., a workstation, a computer, a tablet, a personal communication device such as a smartphone, etc.) is used to improve the performance of an ischemia monitoring ECG algorithm executed by the ECG analysis component 20. Ischemia monitoring ECG algorithms typically monitor the voltage level of the ST-segment of the QRS-T ECG complex. In the simplest example, ST-segment elevation above 100 μV can be used as a threshold to detect ischemia; however, other non-ischemic conditions can cause ST segment elevation of that amount or higher. A well trained ECG reader can recognize the ECG pattern of ST confounder conditions that could go undetected by the untrained ECG algorithm. The user-feedback can be utilized as confirmation of a condition that represents an ST elevation confounder, such as benign early repolarization, acute pericarditis, left ventricular hypertrophy, left bundle branch block, right bundle branch block or the like. The ischemia monitoring ECG algorithm employs the user feedback information to modify its behavior in a number of ways. One such modification to reduce false positive alerts is to switch from alerting on absolute ST elevation to alerting on relative changes in ST elevation. According to another embodiment, algorithm behavior is adjusted to reset the ST baseline for ST thresholds to the ST values found at the time of the user feedback, which also reduces the number of false positive alerts.

Figure 2:
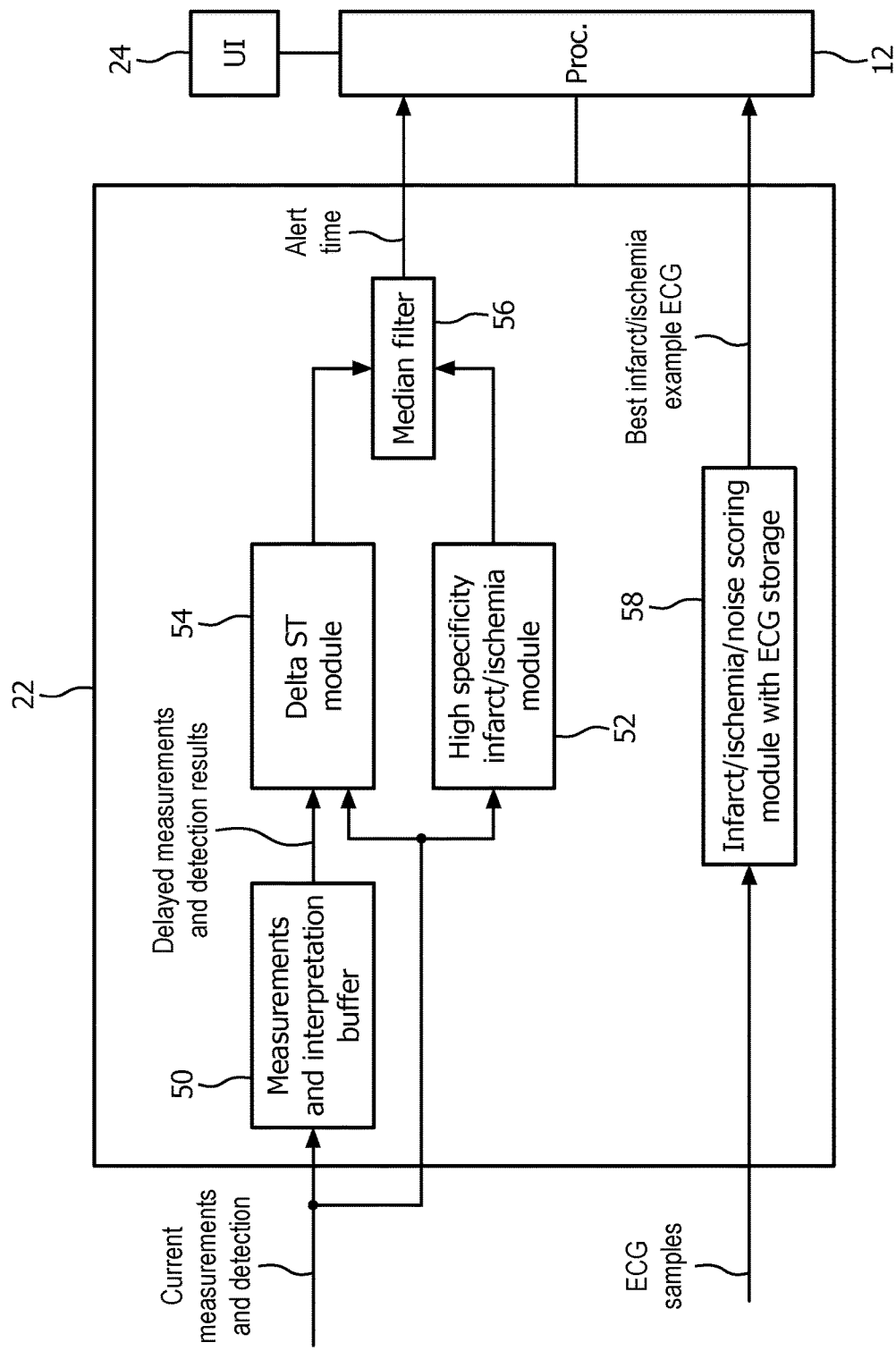
FIG. 2 illustrates a block diagram of the alert generator in accordance with one or more features described herein.

FIG. 2 illustrates a block diagram of the alert generator 22 in accordance with one or more features described herein. Measurements and detection results are stored in one or more circular buffer(s) 50 to implement a "rolling" reference. Multiple buffers can be employed to store and/or delay data for comparison on different time scales. For instance, a first buffer can store data on a scale of minutes, a second buffer on a scale of hours, a third buffer on a scale of days, etc. A high specificity infarction and ischemia detection module 52 in parallel with a ST-elevation change detection module 54 feeds detection results to a modified median filter 56. The results are smoothed and combined by the median filter to trigger alerts for the clinical user. Concurrently, each ECG sample triggering a single infarct/ischemia detection is analyzed by an infarction and ischemia noise detection module 58 to generate a probability score that indicates a likelihood that the detected ischemia pattern is indicative of an ischemic or infarction event and not merely a false positive alert triggered by a confounding condition. The higher the probability of ischemia, the more likely the ECG segment is to be presented to the user as the ECG best representing the alert condition.

With continued reference to FIGS. 1 and 2, the ischemia monitoring system 10 and/or the associated processor 12 is configured to perform several functions, including but not limited to: constructing a representative low noise "beat" including P-wave, QRS, ST-segment and T-wave; measuring parameters of the representative beat related to cardiac ischemia, such as ST-segment voltage, T-wave voltage, Q-wave amplitude and duration, etc.; detecting acute infarction and ischemia using said measurements; and/or performing ischemia/infarction detection based on absolute measurements and/or relative measurements wherein the difference is measured over time.

Another embodiment relates to employing a reduced number of ECG leads when detecting ischemic and/or infarction events. In one embodiment, ischemia/infarction detection is generally based on 12-lead ECG. According to another embodiment, a modified version of the ischemia/infarction monitoring ECG algorithm facilitates detection of an ischemic or infarction event using on a reduced number of leads; e.g., typical criteria based on "contiguous leads" are changed to single lead criteria. This feature reduces the number of uncomfortable ECG electrodes and wires connected to the patient's torso. In addition, this feature also improves computational overhead and improves processor speed with regard to performing the various functions, methods, procedures, etc., described herein. It will be appreciated that ischemia is detected, e.g., when ST elevation and/or other features of ischemia are detected on a single ECG lead, and that infarction can be detected when ST elevation occurs on two or more contiguous ECG leads coupled to a patient.

In accordance with another embodiment, a user is presented, via the user interface, with a selection of abnormalities to be used by the algorithm when performing ischemia/infarction detection. For instance, clinical users can configure the algorithm to use different ECG abnormalities when detecting ischemic or infarction events. Additionally, various ECG features for ischemia/infarction detection can be employed to exploit different tradeoffs in terms of sensitivity and positive predictive value when considering the detection. The following ECG abnormalities and/or features of ischemia and infarction can be employed alone or in combination: ST-segment elevation, wherein the highest specificity is for acute myocardial infarction detection; upsloping ST-segment depression; ST-segment depression; inverted T-waves; flat T-waves; other abnormalities and/or features.

The systems of FIGS. 1 and 2 can also facilitate providing reference for relative measurements. For instance, delta measurements (e.g., change in ST elevation relative to time) can be based on a reference point in time chosen by the clinical user. The reference time or measurement set can be based on algorithm choice based on noise or patient activity level. Additionally, the reference can be a "rolling time," e.g., a time equal to a fixed time difference such that delta measurements can be calculated between a current ECG sample and an ECG sample from 30 minutes past, or some other predetermined time period. The time duration can be a design parameter or a parameter set by the clinical user.

In another embodiment, an alert is issued to the user notifying of potential ischemia and/or infarction that should be investigated further. In this example, the ischemia monitoring algorithm is executed continuously or periodically on a predetermined schedule. Upon detection of ischemia and/or infarction, a decision to generate an alert is based on many detection results over a period of, e.g., minutes (e.g., on the order of 1 to 30 minutes, or some other suitable time frame). The alert can be issued as a pop up window, an icon, an email, a text message, or any other form of communication medium where text messages are delivered nearly instantaneously. To further this example, the alert contains text indicating that ischemia or infarction is suspected and the clinician (e.g., an operator, nurse, monitoring technician, physician, or the like) should order or take an immediate 12-lead ECG for the patient. The alert can also contain a representative ECG to permit the clinician to determine whether it is a false positive alert.

With regard to the representative ECG for detected or suspected infarction and or ischemia, since the ischemia monitoring algorithm takes seconds or minutes to make an optimal decision for an alert, there can be a plurality of ECG strips or segments where ischemia and/or infarction is detected, and it may be impractical to present all ECGs to the clinician for review. For convenience, in this example, a single representative ECG can be passed to the clinician for review. As the ischemia monitoring algorithm is executed, it stores e.g. a 10 sec ECG or an ECG "strip" each time ischemia or infarction is detected. The stored ECG strips are scored based on probability of ischemia and noise content for the quality of the sample they provide to represent ischemia or infarction. When an alert is issued, the ECG sample with the highest probability of ischemia and/or infarction is incorporated as part of the alert output.

In another embodiment, the alert comprises an input means for the clinician to provide feedback to the algorithm, in order to train the algorithm. The feedback may include without limitation: diagnosis of an ST elevation confounder such as left bundle branch block, right bundle branch block, intra-ventricular conduction defect, benign early repolarization, acute pericarditis, left ventricular hypertrophy, or any other ST elevation confounder; diagnosis of heart rhythm that rules out or makes ischemia detection difficult, such as atrial flutter; a button or menu selection indicating a "false alert"; selectable button(s) or menu options to indicate the representative ECG should be used as a reference for ECG features such as ST-segment deviation, T-wave amplitude, Q-wave amplitude/duration, or the like; etc.

For a diagnosis which was undetected by the alert generator module 22, the alert generator module 22 can, e.g., refrain from using absolute ST-deviation thresholds and switch to using relative ST-deviation thresholds, such that ST elevation must increase above the current level to indicate ischemia or infarction. In another embodiment, the alert generator module reverts from absolute Q-wave measurements (e.g., measurements that are a feature of ischemia/infarction detection) to relative Q-wave measurements. In another embodiment, the alert generator module switches from a general set of ischemia/infarction ECG criteria to a set of ECG criteria specific to the ST confounder or diagnosis selected or input by the clinical user.

Figure 3:
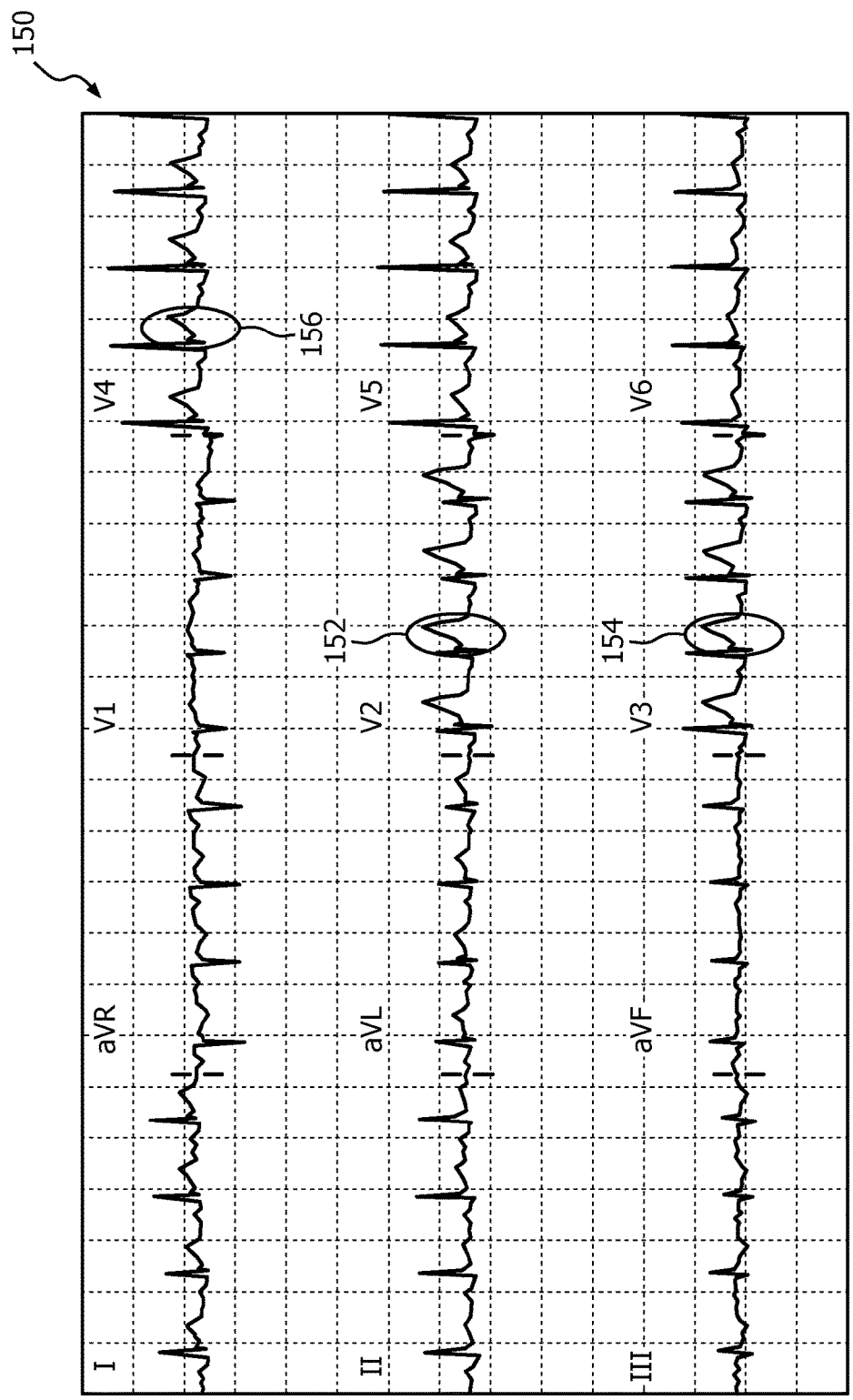
FIG. 3 shows an example of an ECG wherein a confounder condition causes ST segment elevation that can be rejected via user input to train the alert generator module in order to mitigate false positive alerts indicating ischemic and/or infarction events, in accordance with one or more aspects described herein.

FIG. 3 shows an example of an ECG 150 wherein a confounder condition (early repolarization, or "ER" in this example) causes ST segment elevation that can be rejected via user input to train the alert generator module 22 (FIGS. 1 and 2) in order to mitigate false positive alerts indicating ischemic and/or infarction events, in accordance with one or more aspects described herein. In one example, the feedback provided by the user (clinician) is fed directly to the alert generator 22 (see, e.g., FIGS. 1 and 2), and used by the processor to reconfigure or adjust the ischemia detection ECG algorithm executed thereby.

As can be seen in FIG. 3, the ECG shows high levels of ST elevation 152, 154, 156 in respective chest leads V2, V3, an V4. However, these ST segment elevations are not indicative of acute myocardial infarction, but rather the result of early repolarization of the myocardium. If the elevated ST segment from leads V2, V3, and/or V4 triggers an alert by the alert generator module, a clinician can enter feedback (e.g., via a user input device, user interface, drop down menu, or the like) to indicate that the elevated ST segments and other features that triggered the alert are in fact indicative of early repolarization and not infarction. The user input is then employed by the processor (FIG. 1) to train, refine, or adjust the ischemia detection algorithm executed by the alert generator module and/or the processor in order to mitigate false positive alerts due to early repolarization (or any other confounding condition that may be mistaken for an elevated ST segment indicative of infarction or ischemia).

Figure 4:
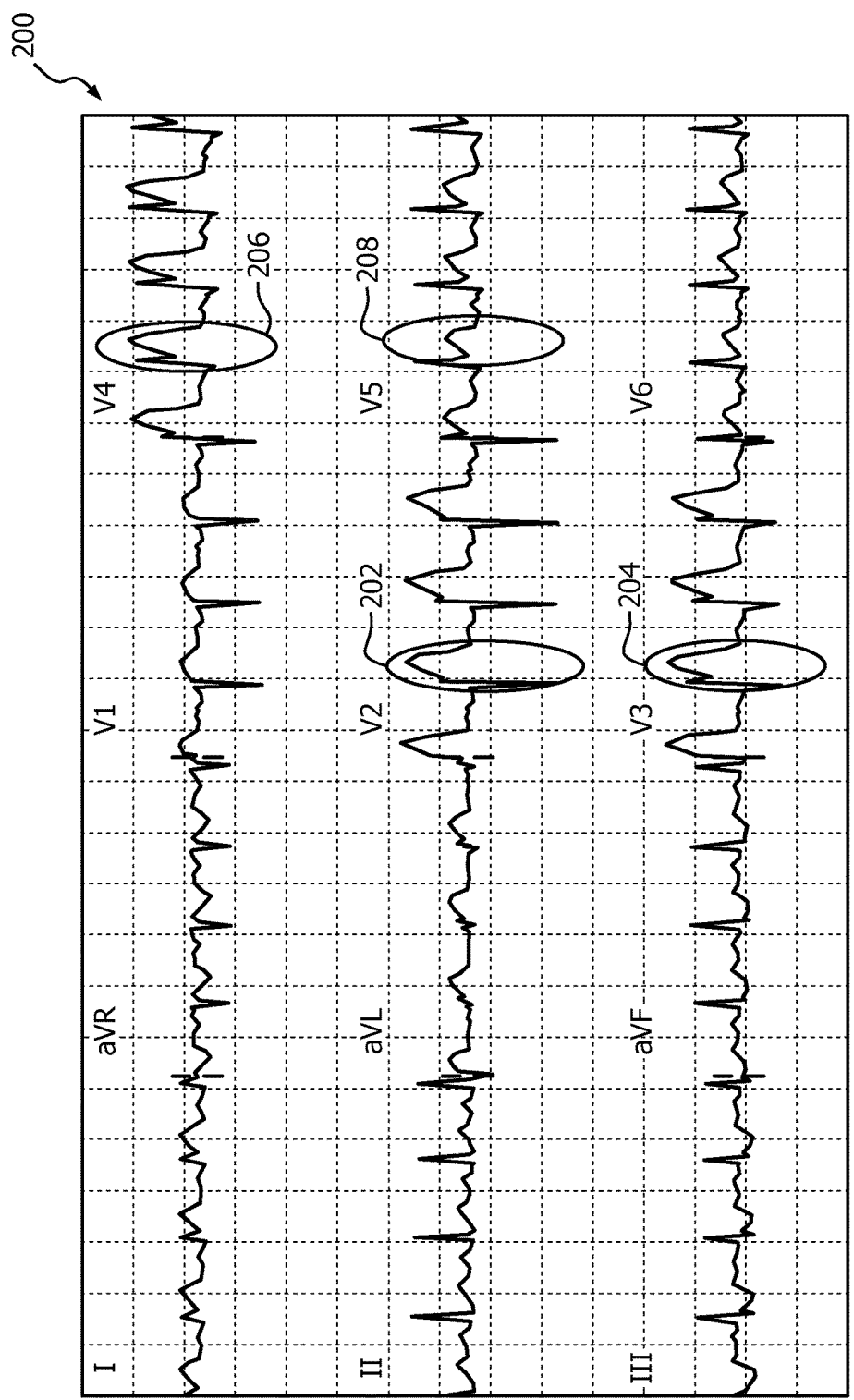
FIG. 4 shows an example of an ECG wherein an ischemic event or infarction event causes ST elevation that is detected to generate an alert, in accordance with one or more features described herein.

FIG. 4 shows an example of an ECG 200 wherein an ischemic event or infarction event causes ST elevation that is detected to generate an alert, in accordance with one or more features described herein. As can be seen, ST segment elevation 202, 204, 206, 208 is clear in respective chest leads V2, V3, V4, V5, and is indicative of acute myocardial infarction. In this case, a clinician can verify to the alert generator module 22 (FIGS. 1 and 2) that the alert is not a false positive, or can refrain from providing corrective input since the alert is not a false positive.

In another embodiment, if the patient is too unstable to be treated for cardiac ischemia, or the treatment is drugs only, the patient may continue to be monitored with no invasive intervention. The systems and methods described herein can track the ischemia status of the patient and provide reports of the ischemic burden, e.g., how many hours the patient showed signs of ischemia, the time of ischemia onset, the duration of the ischemia, etc.

Figure 5:
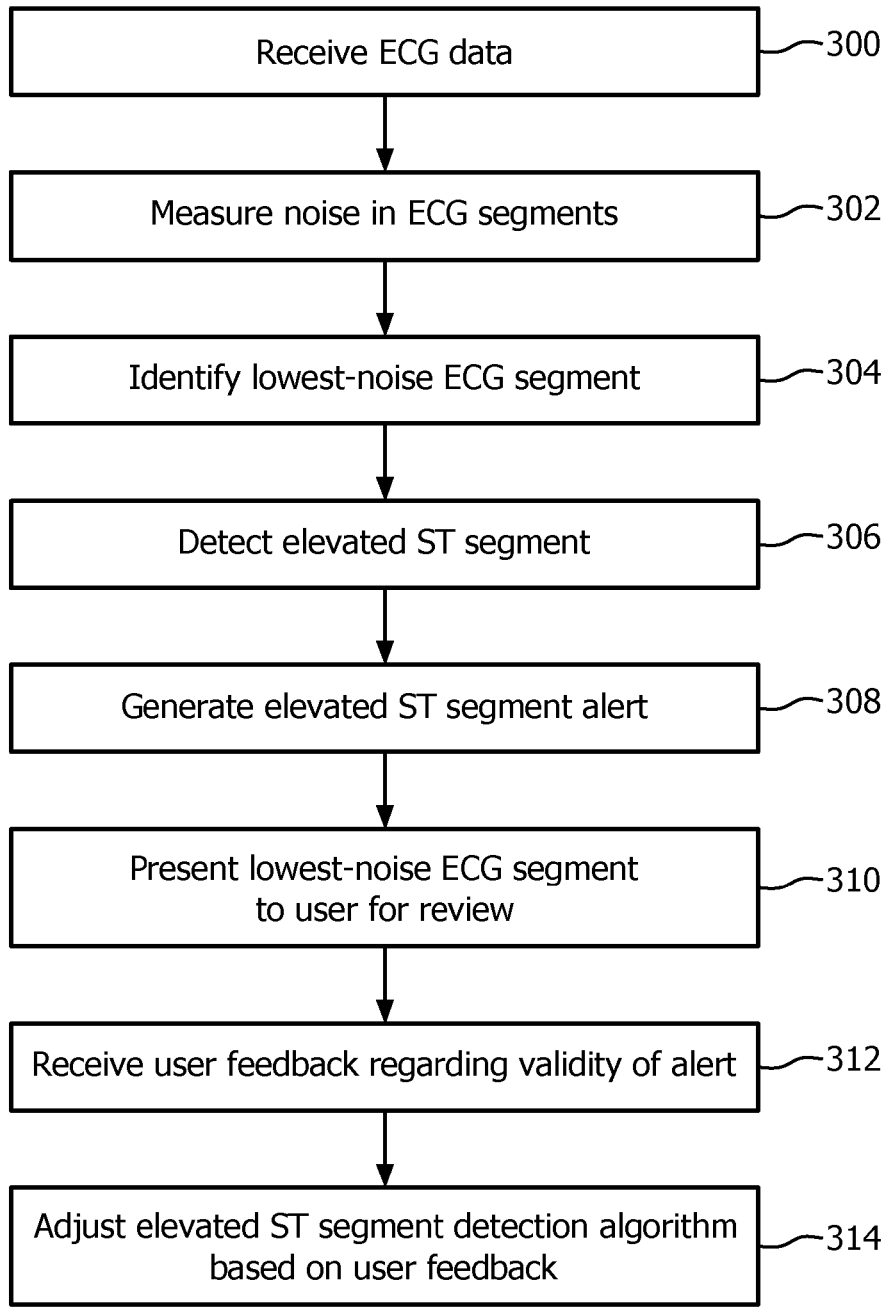
FIG. 5 illustrates a method for mitigating false positive alerts for elevated ST segments (and other ischemic features and patterns) in an ECG indicative of ischemia or myocardial infarction, in accordance with various features described herein.

FIG. 5 illustrates a method for mitigating false positive alerts for elevated ST segments in an electrocardiogram (ECG) indicative of ischemia or myocardial infarction, in accordance with various features described herein. At 300, real-time ECG data is received. At 302, a level of noise associated with each of a plurality of ECG segments is measured. At 304, a lowest-noise ECG segment is identified, which has a lowest level of noise relative to other ECG segments in the plurality of ECG segments. At 306, the lowest-noise ECG segment is analyzed to detect one or more elevated ST segments therein. At 308, upon detection of the one or more elevated ST segments, an alert is generated. The lowest-noise ECG segment that triggered the alert is presented to a user for review, at 310. At 312, user feedback regarding whether the alert is a false positive is received. At 314, an elevated ST segment detection algorithm is adjusted as a function of the received user input such that elevated ST segments not indicative of ischemia or myocardial infarction are ignored.

According to one embodiment, the elevated ST segment is detected by comparing absolute ST elevation to a predetermined ST elevation threshold. According to another embodiment, the elevated ST segment is detected by comparing relative ST elevation over predetermined time period to a predetermined ST elevation threshold. Additionally, the method may comprise presenting a menu of selectable ST-elevating conditions on a user interface and receiving the user input via the user interface. The selectable ST-elevating conditions can include ischemia, myocardial infarction, and one or more confounding conditions that cause elevated ST segments but are not indicative of ischemia or myocardial infarction. For instance, the one or more confounding conditions comprise at least one of: left bundle branch block; right bundle branch block; intra-ventricular conduction defect; benign early repolarization; acute pericarditis; left ventricular hypertrophy, or any other condition that causes ST segment elevation. Additional ECG features of ischemia and infarction may be used beyond just ST segment elevation.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. A method of mitigating false positive alerts for ischemic ECG patterns in an electrocardiogram (ECG) indicative of ischemia or myocardial infarction, comprising:
   receiving real-time ECG data;
   measuring a level of noise associated with each of a plurality of ECG segments;
   identifying a lowest-noise ECG segment, which has a lowest level of noise relative to other ECG segments in the plurality of ECG segments;
   analyzing the lowest-noise ECG segment to detect one or more elevated ST segments therein;
   upon detection of the one or more elevated ST segments, generating an alert;
   presenting the lowest-noise ECG segment that triggered the alert to a user for review;
   receiving user feedback regarding whether the alert is a false positive; and
   adjusting an elevated ST segment detection algorithm as a function of the received user input such that elevated ST segments not indicative of ischemia or myocardial infarction are ignored.

2. The method according to claim 1, wherein the elevated ST segment is detected by comparing absolute ST elevation to a predetermined ST elevation threshold.

3. The method according to claim 1, wherein the elevated ST segment is detected by comparing relative ST elevation over predetermined time period to a predetermined ST elevation threshold.

4. The method according to claim 1, further comprising presenting a menu of selectable ST-elevating conditions on a user interface and receiving the user input via the user interface.

5. The method according to claim 1, wherein the selectable ST-elevating conditions include ischemia, myocardial infarction, and one or more confounding conditions that cause elevated ST segments but are not indicative of ischemia or myocardial infarction.

6. The method according to claim 5, wherein the one or more confounding conditions comprise at least one of:
   left bundle branch block;
   right bundle branch block;
   intra-ventricular conduction defect;
   benign early repolarization;
   acute pericarditis; and
   left ventricular hypertrophy.

7. The method according to claim 1, wherein the ECG patterns comprise one or more of:
   elevated ST segments;
   ST depression;
   inverted T-waves;
   pathologic Q-waves; and
   reduced R-waves.

8. The method according to claim 1, further comprising:
   determining at least one of patient condition being unstable such that invasive treatment for cardiac ischemia is not permitted, or that a non-invasive cardiac ischemia treatment comprises medication only;
   continuing monitoring of the patient with no invasive intervention;
   tracking ischemia status of the patient; and providing one or more reports on ischemic burden, the reports comprising at least one of a time of ischemia onset and the duration of the ischemia.

9. A processor configured to execute the method according to claim 1.

10. A system that facilitates mitigating false positive alerts when monitoring ST elevation in an electrocardiogram (ECG) indicative of ischemia or myocardial infarction, comprising:
a noise measurer configured to receive real-time ECG data and measure a level of noise associated with each of a plurality of ECG segments;
a best periodic ECG identifier configured to receive the real-time ECG data and noise measurement information from the noise measurer, and identify a lowest-noise ECG segment, which has a lowest level of noise relative to other ECG segments in the plurality of ECG segments;
an ECG analyzer configured to analyze the lowest-noise ECG segment to detect one or more elevated ST segments therein;
an alert generator configured to generate an alert upon detection of the one or more elevated ST segments;
a user interface on which the lowest-noise ECG segment that triggered the alert is presented to a user for review and via which the alert generator receives user feedback regarding whether the alert is a false positive; and
a processor configured to adjust an elevated ST segment detection algorithm as a function of the received user input such that elevated ST segments not indicative of ischemia or myocardial infarction are ignored.

11. The system according to claim 10, wherein the alert generator is further configured to detect the elevated ST segment by comparing absolute ST segment elevation to a predetermined ST elevation threshold.

12. The system according to claim 10, wherein the alert generator is further configured to detect the elevated ST segment by comparing relative ST elevation over predetermined time period to a predetermined ST elevation threshold.

13. The system according to claim 10, wherein the processor is further configured to preset a menu, via the user interface, of selectable ST-elevating conditions, and to receive the user input via the user interface.

14. The system according to claim 10, wherein the selectable ST-elevating conditions include ischemia, myocardial infarction, and one or more confounding conditions that cause elevated ST segments but are not indicative of ischemia or myocardial infarction.

15. The system according to claim 14, wherein the one or more confounding conditions comprise at least one of:
a left bundle branch block;
a right bundle branch block;
an intra-ventricular conduction defect;
benign early repolarization;
acute pericarditis; and
left ventricular hypertrophy.

16. An alert generator device configured to generate alerts indicative of ischemia or myocardial infarction upon detection of elevated ST segments in an electrocardiogram (ECG), comprising:
at least one measurement buffer configured to receive current ECG segment measurements and elevated ST segment information;
an ST segment elevation change detector configured to receive the current ECG segment measurements and elevated ST segment information and receive delayed measurement and elevated ST segment information from the buffer for comparison;
an infarct and ischemia detector configured to receive the current ECG segment measurements and elevated ST segment information and detect an elevated ST segment;
a median filter configured to receive and combine ST elevation change information from the ST segment elevation change module and the detected elevated ST segment from the infarct and ischemia detection module, and generate an alert as a function of the received outputs; and
an infarct and ischemia noise scorer configured to generate a probability indicative of a likelihood that the detected elevated ST segment is indicative of an ischemic or infarction event and output a predetermined ECG sample segment to a user interface for user confirmation that the alert is not a false positive.

17. The alert generator device according to claim 16, further comprising a processor configured to preset a menu, via the user interface of selectable ST-elevating conditions, and to receive the user input via the user interface.

18. The alert generator device according to claim 16, wherein the selectable ST-elevating conditions include ischemia, myocardial infarction, and one or more confounding conditions that cause elevated ST segments but are not indicative of ischemia or myocardial infarction.

19. The alert generator of claim 16, wherein the at least one measurement buffer comprises a plurality of measurement buffers, each of which stores data for a different time scale.

* * * * *